United States Patent [19]

Kaino et al.

[11] Patent Number: 4,747,014
[45] Date of Patent: May 24, 1988

[54] REDUCTION-REOXIDATION TYPE SEMICONDUCTOR CERAMIC CAPACITOR AND METHOD OF MANUFACTURING THEREOF

[75] Inventors: Daisuke Kaino; Katsuhiko Arai; Junichi Watanabe; Kazuo Sasazawa, all of Tokyo, Japan

[73] Assignee: Taiyo Yuden Kabushiki Kaisha, Tokyo, Japan

[21] Appl. No.: 18,893

[22] Filed: Feb. 25, 1987

[30] Foreign Application Priority Data

Feb. 27, 1986 [JP] Japan ................... 61-42518

[51] Int. Cl.$^4$ .................. H01G 4/10; H01G 7/00
[52] U.S. Cl. .................... 361/321; 29/25.42
[58] Field of Search ............ 361/321; 29/25.41, 25.42; 264/61

[56] References Cited

U.S. PATENT DOCUMENTS

| | | | |
|---|---|---|---|
| 3,124,478 | 3/1964 | Cirkler et al. | 361/321 X |
| 3,157,835 | 11/1964 | Cirkler et al. | 361/321 |
| 3,243,315 | 3/1966 | Markarian et al. | 29/25.42 X |
| 3,264,537 | 8/1966 | Delaney et al. | 361/321 X |
| 3,274,467 | 9/1966 | Graf | 361/321 |
| 4,097,911 | 6/1978 | Dorrian | 361/321 X |
| 4,486,813 | 12/1984 | Maher | 361/321 |
| 4,490,318 | 12/1984 | Masuyama et al. | 264/61 |

Primary Examiner—Donald A. Griffin
Attorney, Agent, or Firm—Flynn, Thiel, Boutell & Tanis

[57] ABSTRACT

A reduction-reoxidation type semiconductor ceramic capacitor according to the first invention includes: semiconductor ceramic; a reoxidated dielectric layer formed on the surface of the semiconductor ceramic; at least a pair of electrodes formed on the reoxidated dielectric layer; one of the electrodes being formed with an electrical conductor containing one kind or more of metals or metal compounds selected from Zn, Al, Ni, and Sn; one kind or more of metals in extremely small quantities selected from the metals being diffused into the interior of a portion, in contact with said electrode, of the reoxidated dielectric layer.

In addition, a method of manufacturing of the reduction-reoxidation type semiconductor ceramic capacitor comprising the steps of: rendering the semiconductor ceramic to a heat treatment at temperature of from 950° to 1200° C. to thereby form the reoxidated dielectric layer; providing an electrode material layer containing one kind or more of metals or metal compounds selected from Zn, Al, Ni and Sn on a portion forming one of said electrodes; and baking said electrode material layer so provided at temperature of from 600° to 850° C. to thereby form the electrode.

5 Claims, 1 Drawing Sheet

REDUCTION-REOXIDATION TYPE SEMICONDUCTOR CERAMIC CAPACITOR AND METHOD OF MANUFACTURING THEREOF

BACKGROUND OF THE INVENTION

1. Field of the Invention

The present invention relates to a ceramic capacitor and manufacturing thereof, which profitably employs as a dielectric substance a reoxidated layer formed on the surface of a reduced semiconductor ceramic by reoxidating the reduced semiconductor ceramic.

2. Description of the Prior Art

Prior reduction-reoxidation type semiconductor ceramic capacitors are substantially classified into two types. One is, as illustrated in FIG. 4, adapted to heat-treat semiconductor ceramic 1 to thereby form a reoxidated dielectric layer on the surface of the semiconductor ceramic 1 as a dielectric layer 2, and thereafter dispose a pair of electrodes 3, 4 on the dielectric layer 2 in confronting relation. The other is adapted to employ as an electrode material electrode paste containing glass frit without rendering a semiconductor ceramic to a reoxidation treatment, and to diffuse in vapor phase, upon baking the electrode paste, a glass frit component contained in the electrode paste onto the surface of the semiconductor ceramic for forming a barrier layer as a dielectric layer on the surface of the semiconductor surface.

Such a reduction-reoxidation type semiconductor ceramic capacitor, which assured an extremely thin dielectric layer 2, was developed as a capacitor providing large electrostatic capacity. However, the structure shown in FIG. 4 permits the semiconductor layer 1 to be located between the electrodes 3, 4 on both sides thereof and functions as another electrode holding the dielectric layer 2 therebetween. Accordingly, the structure appears as if there exist two capacitors connected in series to each other, and hence is limited in its electrostatic capacity.

Against this, many efforts were exerted to investigate other types of reduction-reoxidation type semiconductor ceramic capacitors for the purpose of obtaining further larger electrostatic capacity. For example, there were developed those having the dielectric layer 2 only on a portion which makes contact with any one electrode 4 between a pair of electrodes 3, 4 provided on the semiconductor ceramic 1.

To be concrete, the following two types of capacitors are considered: one is, as illustrated in FIG. 5, adapted to previously heat-treat semiconductor ceramic 1 to form on the surface thereof a reoxidation layer as part of a dielectric layer 2, and remove part of the dielectric layer 2 by polishing, and furthermore to place electrodes 3, 4 respectively on the remaining dielectric layer 2 and on the semiconductor ceramic 1 exposed by the above polishing; the other is adapted to employ, upon baking the electrode 4 when forming the same, electrode paste containing metal or a metal compound serving to prevent a barrier layer from being formed on the surface of the semiconductor ceramic 1, and to render the electrode paste to baking together with the other electrode 3.

However, the former suffered from problems of, upon increasing the productivity, the increased number of fabrication processes accompanying fine polishing of the semiconductor ceramic 1 as well as increased troubles attendant on the damaged semiconductor ceramic 1. In addition, in the latter case, a barrier layer can be formed on the surface of the semiconductor ceramic 1 at the temperature of baking of the electrodes 3, 4, but it is difficult in fact to provide a sufficiently thick dielectric layer 2. For this reason there appears such a rectification effect by the action of the barrier layer that the amount of a current flowing therethrough is extremely different depending on the polarities of voltage applied between the electrodes 3, 4.

SUMMARY OF THE INVENTION

In view of the drawbacks attendant on the conventional reduction-reoxidation type semiconductor ceramic capacitors and the fabrication thereof, it is an object of the present invention to solve these aforementioned problems.

In what follows, the arrangement of the present invention will be described with reference to FIGS. 1 and 2.

First, a reduction-reoxidation type semiconductor ceramic capacitor according to the first invention consists of: semiconductor ceramic 11; a reoxidated dielectric layer 12 formed on the surface of the semiconductor ceramic 11; at least a pair of electrodes 13, 14 being formed on the reoxidated dielectric layer 12; one 14 of the electrodes 13, 14 being formed with an electrical conductor containing one kind or more of metals or metal compounds selected from Zn, Al, Ni, and Sn; with one or more metals, in extremely small quantities, from the above metals being diffused into the interior of a portion, in contact with the electrode 14, of the reoxidated dielectric layer 12.

In addition, a method of manufacturing the aforesaid ceramic capacitor according to the second invention consists of: rendering the semiconductor ceramic 11 to a heat treatment at temperature of from 950° to 1200° C. to thereby form the reoxidated dielectric layer 12; providing an electrode material layer containing one kind or more of metals or metal compounds selected from Zn, Al, Ni, and Sn on a portion of the dielectric layer and forming one 14 of the electrode 13, 14; and baking the electrode material layer so provided at temperature of from 600° to 850° C. to thereby form the electrode 14.

According to the second invention, the semiconductor ceramic 11 are rendered to a heat treatment at temperature of from 950° to 1200° C. to thereby re-oxidate the whole surface of the semiconductor ceramic for forming the reoxidated dielectric layer 12 having its thickness of about 10μ.

Thereafter, when the electrode material layer is formed on the reoxidated semiconductor layer 12, which is in turn baked to form the electrodes 13, 14, oxygen existent in the reoxidated dielectric layer 12 is extracted therefrom by the action of reduction of the one kind or more of those metals or metal compounds selected from Zn, Al, Ni and Sn contained in the one 14 of the electrode materials. Simultaneously, the one kind or more of those metals in extremely small quantities selected from Zn, Al, Ni, and Sn are diffused into the interior of the semiconductor ceramic 11. Hereby, a reduction-reoxidation type ceramic capacitor according to the first invention can be yielded.

The resulting reduction-reoxidation type ceramic capacitor is adapted to permit the semiconductor ceramic 11 and the electrode 14 to be connected with each other in an electrically conductive manner without interposition of the reoxidated dielectric layer 12.

Therefore, the electrodes 13 and 14 are substantially adapted to face each other while holding one layer of the reoxidated dielectric layer 12 therebetween in a sandwitching relation to assure large electrostatic capacitance.

Moreover, in the second invention, the temperature of a heat treatment upon rendering the semiconductor ceramic 11 to a reoxidation treatment was limited within the range of from 950° to 1200° C., the reason of which is as follows: provided the temperature lies below the above temperature range, the surface of the semiconductor ceramic 11 is reoxidated insufficiently to provide satisfactory insulating characteristics. Contrary, to the heat treatment temperature exceeding this temperature range, the reoxidation of the semiconductor ceramic 11 is extremely speeded up to result in the thickness of the reoxidated dielectric layer 12 located on the surface of the semiconductor ceramic 11 being increased in excess, and thus large electrostatic capacity is unlikely to be obtained.

Furthermore, the heat treatment temperature upon baking the electrodes 13, 14 was limited within the range of from 600° to 850° C., the reason of which is as follows: provided the heat treatment temperature lies below this range, reduction on the side of the electrode 14 and diffusion of the metal components into the reoxidated semiconductor layer 12 are difficult to be effected, and hence large electrostatic capacity is unlikely to be obtained. By contrast, with the heat treatment temperature exceeding this temperature range, the electrode 14 is reoxidated to result in an undesirable increase of electric resistance with the possibility of a function thereof as an electrode being not obtainable.

The above and other objects, features and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
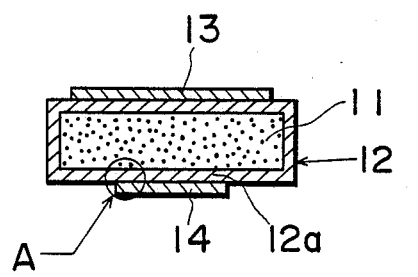
FIG. 1 is a longitudinal cross sectional view of a reduction-reoxidation type semiconductor ceramic capacitor, enlarged in a thickness direction, illustrating an embodiment of the first invention.

In what follows, embodiments of a reduction-reoxidation type semiconductor ceramic capacitor according to the present invention will be described with reference to the accompanying drawings.

(Embodiments 1 to 6)

As embodiments of 1 to 6, a reduction-reoxidation type semiconductor ceramic capacitors of one hundred for each embodiment were manufactured in conformity with conditions listed in Table 1 for samples of Nos. 1 to 6 in the following procedures, respectively.

First, material powders were measured to provide 100 mol of $BaTiO_3$, 3 mol of $Na_2O_3$, 6 mol of $TiO_2$, and 0.5 mol of MnO, and wet blended for 15 hours in a ball mill. These material powders were calcinated for 2 hours at 1150° C., and again wet blended for 15 hours in a ball mill.

Then, the material powders so treated were granulated by addition of polyvinyl alcohol, and molded into disks with 8.4 mm diameter and 0.5 mm thickness. The resulting molded materials were heat-treated for 3 hours at 1350° C. in the atmosphere and furthermore for 2 hours at 1150° C. in the reducing atmosphere of $N_2$—$H_2$ gas to yield a semiconductor ceramic 11.

In succession, the resulting semiconductor ceramic 11 were heat-treated in the atmosphere for 2 hours respectively at temperatures of from 950° to 1200° C. listed in columns of the embodiments of 1 to 6 in Table 1 to reoxidate the surfaces of the semiconductor ceramic for forming reoxidated dielectric layers 12.

In addition, electrodes 13, 14 were formed by applying a pasty electrode material on opposing main surfaces of the semiconductor ceramic 11 from the upper of the reoxidated dielectric layers 12, and heat-treating the semiconductor ceramic 11 for 30 minutes at 800° C. to bake the electrode materials. Thereupon, electrically conductive paste was employed as an electrode material for the electrode 13, which comprises 10 parts by weight of glass powder of $PbO$—$B_2O_3$—$SiO_2$ and 20 parts by weight of an organic binder with respect to 100 parts by weight of Ag powder, while electrically conductive paste was likewise employed for the electrode 14, which comprises 10 parts by weight of $PbO$—$B_2O_3$—$SiO_2$ glass powder and 20 parts by weight of an organic binder with respect to 100 parts by weight of Zn powder.

Figure 2:
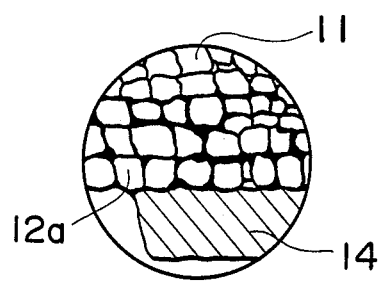
FIG. 2 is an enlarged view of a portion A of FIG. 1.

As described above, reduction-reoxidation type semiconductor ceramic capacitors according to the first invention having a structure illustrated in FIGS. 1 and 2 were respectively manufactured one hundred to every embodiments. Hereupon, in FIG. 1 designated at 12a is a layer, a portion of the reoxidated dielectric layer 12 into which metal is diffused, and FIG. 2 is a schematical view illustrating a state of the same layer 12a, into particle fields of which a metal component is diffused.

Moreover, compositions of the electrode materials employed for the formation of the electrodes 13, 14 prepared as described above are first in columns corresponding to sample Nos. 1 to 6 in Table 1 together with the heat treatment temperatures in the respective manufacturing processes of the above capacitors.

After every 100 capacitors of the embodiments 1 to 6 were left for 3 hours in a room temperature, AC voltage was applied to the electrodes 13, 14 at 25° C. for measuring electrostatic capacitance C and dielectric losses tan δ thereof and for thereby estimating electrostatic capacities C/A [nf/cm$^2$] per unit area of the electrodes 13. In addition, one hundred of the above capacitors were randomly divided into two sets, and 50 V DC voltage was applied, taking the side of the electrode 13 as a negative potential (direction A) or as a positive potential (direction B), to every 50 capacitors for 20 seconds from each direction for measuring insulating resistances IR [MΩ] thereof.

Successively, these capacitors were heat-treated for 30 minutes in a constant temperature both at 150° C., and DC voltage was likewise applied to every 50 capacitors at 125° C. from the directions A and B for measuring insulating resistances IR thereafter. Moreover, with DC voltage applied to every capacitors from the directions A and B, breakdown voltages $V_{BD}$ (voltages when a current of 10 mA is conducted through the samples) were measured.

The mean values of these measurements yielded by these tests are listed in columns of Table 2 corresponding to the sample Nos. 1 to 6.

(Embodiments 7 to 11)

Reduction-reoxidation type semiconductor ceramic capacitors of one hundred to every embodiments were manufactured as embodiments 7 to 11 as listed in Table 1 as sample Nos. 7 to 11 by taking the heat-treatment temperatures of reoxidating the semiconductor ceramic 11 as 1050° C., changing the baking temperatures of the electrodes to the range of from 600° to 850° C., and assuming the other requirements to be the same as in the aforementioned embodiments 1 to 6.

Furthermore, these capacitors were tested in the same manner as in the aforementioned embodiment 1. The mean values of the resulting measured values are listed in columns of Table 2 corresponding to the sample Nos. 7 to 11.

(Embodiments 12 to 15)

Reduction-reoxidation type semiconductor ceramic capacitors of one hundred to every embodiments were manufactured as embodiments 12 to 15 as listed in Table 1 as sample Nos. 12 to 15 by taking the reoxidation heat-treatment temperatures as 1050° C., the baking temperatures of the electrodes as 800° C., changing compositions of electrode materials for use in the electrodes 14, and assuming the other requirements to be the same as in the aforementioned embodiments 1 to 6.

In addition, these capacitors were tested in the same manner as in the above embodiment 1. The mean values of the resulting measured values are listed in columns of Table 2 corresponding to the sample Nos. 12 to 15.

(Embodiment 16)

Reduction-reoxidation type semiconductor ceramic capacitors of one hundred were manufactured as an embodiment 16 as listed in Table as a sample No. 16 by taking the re-oxidation treatment temperature as 1050° C. and the electrode baking temperature as 800° C., employing known ohmic Ag electrode paste containing In-Ga as the electrode materials for forming the electrodes 13, and assuming the other requirements to be the same as in the aforementioned embodiments 1 to 6.

In addition, these capacitors were tested in the same manner as in the aforementioned embodiment 1. The mean values of the resulting measured values are listed in columns of Table 2 corresponding to the sample No. 16.

(Comparison 1)

Reduction-re-oxidation type semiconductor ceramic capacitors of one hundred were manufactured as a comparison 1 as listed in Table 1 as sample No. 17 without conducting the reoxidation treatment of the semiconductor ceramic 11, by assuming the other requirements to be the same as in the aforementioned embodiments 1 to 6.

In addition, these capacitors were tested in the same manner as in the aforementioned embodiment 1. The mean values of the resulting measured values are listed in the column of the sample No. 17 in Table 2.

(Comparison 2)

Reduction-reoxidation type semiconductor ceramic capacitors of one hundred were manufactured as a comparison 2 as listed in Table 1 as the sample No. 18 by taking the reoxidation treatment temperature for the semiconductor ceramic 11 as 900° C., and assuming the other requirements to be the same as in the aforementioned embodiments 1 to 6.

Moreover, these capacitors so manufactured were tested in the same manner as in the aforementioned embodiment 1. The mean values of the resulting measured values are listed in the column of the sample No. 18 in Table 2.

(Comparison 3)

Reduction-reoxidation type semiconductor ceramic capacitors of one hundred were manufactured as a comparison 3 as listed in Table 1 as the sample No. 19 by taking the electrode baking temperature for the semiconductor ceramic 11 as 900° C. and assuming the other requirements to be the same as in the aforementioned embodiments 1 to 6.

In addition, these capacitors so manufactured were tested in the same manner as in the aforementioned embodiment 1. The mean values of the resulting measured values are listed in the column of the sample No. 19 in Table 2.

As evidenced from Table 2, there is found no rectification effect, the effect exerting a current value being extremely different depending on the direction of voltage applied to the electrodes 13, 14, in those reduction-reoxidation type semiconductor ceramic capacitors of the embodiments 1 to 16 yielded according to the present invention. Against this, in those capacitors of the comparison 1 wherein the barrier layer is formed at the interface between the electrodes 13, 14 and the semiconductor ceramic 11 without the reoxidation treatment for the semiconductor ceramic 11, no rectification effect, the effect exerting a current value being shaply different depending on the direction of voltage applied to the electrodes, is found as to insulating characteristics, particularly as to insulation resistance and dielectric strength at high temperature.

In addition, in the embodiments 1 to 16 the breakdown voltages $V_{BD}$ were 300 V or more in either direction of the voltage application, but in the comparison 2 wherein the heat treatment temperature upon the reoxidation was less than 950° C., the reoxidation of the surface of the semiconductor ceramic 11 was insufficient, and hence the breakdown voltage $V_{BD}$ particularly in the direction B was extremely low and impossible to measure.

Moreover, in the comparison 3 wherein the heat treatment temperature upon baking of the electrodes was 900° C., the electrode layer 14 to exert a reducing action was oxidated to provide high resistance, and hence demonstrated no function as an electrode.

Figure 3:
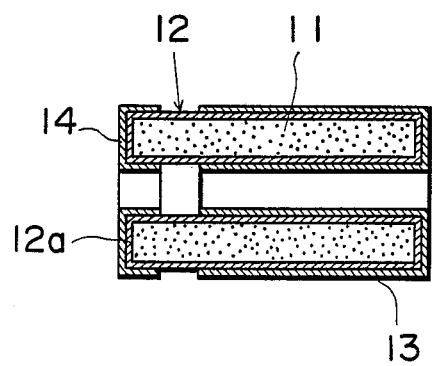
FIG. 3 is a longitudinal cross sectional view of a reduction-reoxidation type semiconductor ceramic capacitor illustrating another embodiment of the first invention.
Figure 4:
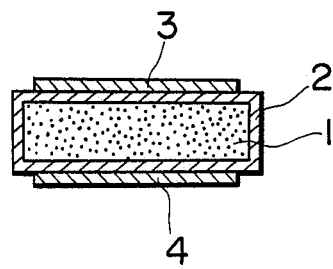
FIGS. 4 and 5 are longitudinal cross sectional views respectively illustrating prior reoxidation type semiconductor ceramic capacitors.
Figure 5:
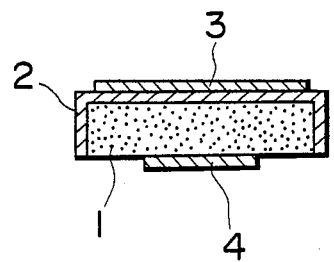

Furthermore, all the aforementioned embodiments employed, as means to form the electrode 13, means for applying a pasty electrode material on the semiconductor ceramic 11 and baking it, but another methods to form the electrode 13 other than this means, for example those of electroless plating, deposition, and vacuum impregnation also assure the same action and effect. Furthermore, it is also possible to employ, as the shape of the semiconductor ceramic 11, a cylindrical one for example as shown in FIG. 3 in addition to the diskshaped one shown in FIG. 1 for providing the electrodes 13, 14 on the inner and outer peripheral surfaces of this cylindrical one.

According to the first and second inventions, as described above, large electrostatic capacity and hence large capacity capacitors can be yielded with ease without polishing the semiconductor ceramic 11.

Furthermore, according to the second invention, it is possible to form, upon manufacturing the reduction-reoxidation type semiconductor ceramic capacitor according to the first invention, a sufficiently thick reoxidated dielectric layer on the surface of the semiconductor ceramics 11, and hence no rectification effect, the effect exerting current values extremely different depending on the positive or negative direction of voltage applied between the electrodes 13, 14 is produced for thereby improving reliability.

Although certain preferred embodiments and comparisons have been shown and described, it should be understood that many changes and modifications may be made therein without departing from the scope of the appended claims.

What is claimed is:

1. A reduction-reoxidation semiconductor ceramic capacitor comprising:

(a) a semiconductor ceramic body having opposite surfaces;
(b) reoxidated dielectric ceramic layers formed on said surfaces of said semiconductor ceramic body; and
(c) at least a pair of electrodes formed on the surfaces of said reoxidated dielectric ceramic layers, wherein one of said electrodes is made of an electrically conductive material containing at least one substance selected from the group consisting of Zn, Al, Ni, Sn and compounds thereof, and extremely small quantities of said at least one substance being diffused into the interparticle spaces in the interior of the adjacent reoxidated dielectric ceramic layer so that said semiconductor ceramic body and said one electrode are directly electrically connected with each other by means of said at least one substance.

2. The semiconductor ceramic capacitor of claim 1 wherein said semiconductor ceramic comprises $BaTiO_3$, $Na_2O_3$, $TiO_2$ and MnO, one of the electrodes comprises Zn, PbO, $B_2O_3$ and $SiO_2$ and the other electrode comprises Ag, PbO, $B_2O_3$ and $SiO_2$.

TABLE 1

| Sample NO. | Heat Treatment Temperature for Ceramics | | Composition of Electrode | | Baking Temperature of Electrode |
|---|---|---|---|---|---|
| | Reduction | Re-oxidation | Electrode 4 | Electrode 3 | |
| 1 | 1150° C. | 950° C. | Zn,Pb—B—Si | Ag,Pb—B—Si | 800° C. |
| 2 | 1150° C. | 1000° C. | Zn,Pb—B—Si | Ag,Pb—B—Si | 800° C. |
| 3 | 1150° C. | 1050° C. | Zn,Pb—B—Si | Ag,Pb—B—Si | 800° C. |
| 4 | 1150° C. | 1100° C. | Zn,Pb—B—Si | Ag,Pb—B—Si | 800° C. |
| 5 | 1150° C. | 1150° C. | Zn,Pb—B—Si | Ag,Pb—B—Si | 800° C. |
| 6 | 1150° C. | 1200° C. | Zn,Pb—B—Si | Ag,Pb—B—Si | 800° C. |
| 7 | 1150° C. | 1050° C. | Zn,Pb—B—Si | Ag,Pb—B—Si | 600° C. |
| 8 | 1150° C. | 1050° C. | Zn,Pb—B—Si | Ag,Pb—B—Si | 650° C. |
| 9 | 1150° C. | 1050° C. | Zn,Pb—B—Si | Ag,Pb—B—Si | 700° C. |
| 10 | 1150° C. | 1050° C. | Zn,Pb—B—Si | Ag,Pb—B—Si | 750° C. |
| 11 | 1150° C. | 1050° C. | Zn,Pb—B—Si | Ag,Pb—B—Si | 850° C. |
| 12 | 1150° C. | 1050° C. | Sn,Pb—B—Si | Ag,Pb—B—Si | 800° C. |
| 13 | 1150° C. | 1050° C. | Ni,Pb—B—Si | Ag,Pb—B—Si | 800° C. |
| 14 | 1150° C. | 1050° C. | Al,Pb—B—Si | Ag,Pb—B—Si | 800° C. |
| 15 | 1150° C. | 1050° C. | Zn—Al,Pb—B—Si | Ag,Pb—B—Si | 800° C. |
| 16 | 1150° C. | 1050° C. | Zn,Pb—B—Si | In—Ga—Ag,Pb—B—Si | 650° C. |
| 17 | 1150° C. | — | Zn,Pb—B—Si | Ag,Pb—B—Si | 800° C. |
| 18 | 1150° C. | 900° C. | Zn,Pb—B—Si | Ag,Pb—B—Si | 800° C. |
| 19 | 1150° C. | 1050° C. | Zn,Pb—B—Si | Ag,Pb—B—Si | 900° C. |

TABLE 2

| Sample NO. | C/A [nF/cm$^2$] | tanδ [%] | IR [MΩ] Direction | | IR [MΩ] Direction | | $V_{BD}$ [V/10 mA] Direction | |
|---|---|---|---|---|---|---|---|---|
| | | | A | B | A | B | A | B |
| 1 | 850 | 7.8 | $3.3 \times 10^3$ | $3.2 \times 10^3$ | $4.5 \times 10^2$ | $3.6 \times 10^2$ | 425 | 300 |
| 2 | 770 | 6.5 | $4.5 \times 10^3$ | $4.0 \times 10^3$ | $6.5 \times 10^2$ | $6.2 \times 10^2$ | 650 | 600 |
| 3 | 720 | 5.3 | $5.1 \times 10^3$ | $5.3 \times 10^3$ | $7.5 \times 10^2$ | $7.5 \times 10^2$ | 700 | 700 |
| 4 | 640 | 5.0 | $5.5 \times 10^3$ | $5.8 \times 10^3$ | $7.1 \times 10^2$ | $7.2 \times 10^2$ | 750 | 650 |
| 5 | 520 | 4.7 | $6.2 \times 10^3$ | $7.0 \times 10^3$ | $1.0 \times 10^3$ | $1.0 \times 10^3$ | 800 | 800 |
| 6 | 380 | 4.3 | $6.4 \times 10^3$ | $7.0 \times 10^3$ | $1.0 \times 10^3$ | $1.0 \times 10^3$ | 800 | 800 |
| 7 | 400 | 12.4 | $1.0 \times 10^4$ | $8.3 \times 10^3$ | $1.0 \times 10^3$ | $7.8 \times 10^2$ | 800 | 700 |
| 8 | 520 | 10.8 | $8.5 \times 10^3$ | $6.4 \times 10^3$ | $8.2 \times 10^2$ | $8.1 \times 10^2$ | 800 | 750 |
| 9 | 670 | 7.2 | $6.2 \times 10^3$ | $5.3 \times 10^3$ | $7.8 \times 10^2$ | $7.5 \times 10^2$ | 750 | 725 |
| 10 | 720 | 6.1 | $5.8 \times 10^3$ | $5.3 \times 10^3$ | $7.5 \times 10^2$ | $7.5 \times 10^2$ | 750 | 725 |
| 11 | 720 | 5.5 | $5.2 \times 10^3$ | $5.1 \times 10^3$ | $7.5 \times 10^2$ | $7.5 \times 10^2$ | 700 | 700 |
| 12 | 750 | 6.0 | $4.2 \times 10^3$ | $4.4 \times 10^3$ | $7.0 \times 10^2$ | $7.1 \times 10^2$ | 700 | 700 |
| 13 | 720 | 5.3 | $5.0 \times 10^3$ | $5.2 \times 10^3$ | $6.9 \times 10^2$ | $6.8 \times 10^2$ | 650 | 650 |
| 14 | 720 | 5.7 | $4.2 \times 10^3$ | $5.0 \times 10^3$ | $8.1 \times 10^2$ | $7.5 \times 10^2$ | 700 | 675 |
| 15 | 720 | 5.6 | $5.4 \times 10^3$ | $6.2 \times 10^3$ | $7.5 \times 10^2$ | $7.5 \times 10^2$ | 725 | 750 |
| 16 | 730 | 6.5 | $4.8 \times 10^3$ | $4.7 \times 10^3$ | $6.1 \times 10^2$ | $6.9 \times 10^2$ | 650 | 650 |
| 17 | 900 | 10.2 | $5.2 \times 10^2$ | — | $3.1 \times 10^1$ | — | 75 | — |
| 18 | 900 | 8.5 | $2.0 \times 10^3$ | $0.9 \times 10^1$ | $1.2 \times 10^2$ | — | 150 | — |
| 19 | | | Impossible to measure by oxidation of the electrode | | | | | |

3. A method of manufacturing a reduction-reoxidation semiconductor ceramic capacitor, comprising the steps of:
  (a) subjecting a semiconductor ceramic body to heat treatment at a temperature of from 950° to 1200° C. to thereby form an external reoxidated dielectric ceramic layer on said semiconductor ceramic body;
  (b) placing an electrode material layer on said reoxidated dielectric ceramic layer, said electrode material layer containing at least one substance selected from the group consisting of Zn, Al, Ni, Sn and compounds of these metals; and
  (c) baking said electrode material layer at the temperature of from 600° to 850° C., to thereby form an electrode and to diffuse extremely small quantities of said substance into the inter-particle spaces of the portion of said reoxidated dielectric ceramic layer adjacent said electrode so that said semiconductor ceramic body and said electrode are directly electrically connected with each other by means of said substance.

4. The method of claim 3 wherein said semiconductor ceramic comprises $BaTiO_3$, $Na_2O_3$, $TiO_2$ and MnO, said electrode material layer comprises Zn, PbO, $B_2O_3$ and $SiO_2$, the heat treatment of the semiconductor ceramic body is conducted at a temperature of 1050° C., 1150° C. or 1200° C. and the baking of the electrode material layer is conducted at a temperature of 600° C. or 800° C.

5. The method of claim 4 wherein the heat treatment of the semiconductor ceramic is conducted at a temperature of 1050° C. and the baking of the electrode material layer is conducted at a temperature of 600° C.

* * * * *